(12) United States Patent
Ridvan et al.

(10) Patent No.: US 8,779,005 B2
(45) Date of Patent: Jul. 15, 2014

(54) SALTS OF DESVENLAFAXINE AND A METHOD OF THEIR PREPARATION

(75) Inventors: Ludek Ridvan, Prague (CZ); Petr Hruby, Prague (CZ); Stanislav Radl, Kvetnice (CZ); Hana Brusova, Prague (CZ); Lukas Krejcik, Praha-Vinor (CZ); Tomas Pekarek, Prague (CZ); Natalia Csokova, Bratislava (SK); Anna Zerzanova, Libis (CZ)

(73) Assignee: Zentiva k.s., Prague (CZ)

( * ) Notice: Subject to any disclaimer, the term of this patent is extended or adjusted under 35 U.S.C. 154(b) by 348 days.

(21) Appl. No.: 13/146,467

(22) PCT Filed: Feb. 3, 2010

(86) PCT No.: PCT/CZ2010/000010
§ 371 (c)(1),
(2), (4) Date: Oct. 5, 2011

(87) PCT Pub. No.: WO2010/088865
PCT Pub. Date: Aug. 12, 2010

(65) Prior Publication Data
US 2012/0041227 A1     Feb. 16, 2012

(30) Foreign Application Priority Data
Feb. 6, 2009   (CZ) ........................... 2009-69

(51) Int. Cl.
*A61K 31/205*     (2006.01)
*C07C 215/52*     (2006.01)

(52) U.S. Cl.
CPC ............. *A61K 31/205* (2013.01); *C07C 215/52* (2013.01)
USPC ........................... 514/649; 514/554; 564/336

(58) Field of Classification Search
CPC ............................ A61K 31/205; C07C 215/52
USPC .................................. 514/649, 554; 564/336
See application file for complete search history.

(56) References Cited

U.S. PATENT DOCUMENTS

| 4,535,186 A | 8/1985 | Husbands et al. |
| 6,673,838 B2 | 1/2004 | Hadfield et al. |
| 7,001,920 B2 | 2/2006 | Hadfield et al. |
| 7,026,508 B2 | 4/2006 | Winkley et al. |

FOREIGN PATENT DOCUMENTS

| EP | 2119695 | 11/2009 |
| WO | WO 00/76955 | 12/2000 |
| WO | WO 03/048104 | 6/2003 |
| WO | WO 2007/071404 | 6/2007 |
| WO | WO 2007/120923 | 10/2007 |
| WO | WO 2009/053840 | 4/2009 |
| WO | WO 2009053840 A2 * | 4/2009 |
| WO | WO 2009/114685 | 9/2009 |
| WO | WO 2009114685 A2 * | 9/2009 |
| WO | WO 2009/155488 | 12/2009 |
| WO | WO 2009155488 A2 * | 12/2009 |
| WO | WO 2010/008735 | 1/2010 |
| WO | WO 2010008735 A2 * | 1/2010 |

OTHER PUBLICATIONS

Sorbera et al, Desvenlafaxine Succinate, Drugs of the future 2006, 31(4): 304-309.
International Search report, mailed Oct. 19, 2010, for PCT International application No. PCT/CZ2010/000010.

* cited by examiner

*Primary Examiner* — Joseph Kosack
*Assistant Examiner* — Matthew Coughlin
(74) *Attorney, Agent, or Firm* — Pearl Cohen Zedek Latzer Baratz LLP (57) ABSTRACT

The invention deals with new salts of the desvenlafaxine base of formula (I) with oxalic acid, the new salts being the hydrogen oxalate of formula (II) in the proportion of desvenlafaxine:oxalic acid of 1:1 and hemioxalate of formula (III) in the proportion of desvenlafaxine:oxalic acid of 2:1.

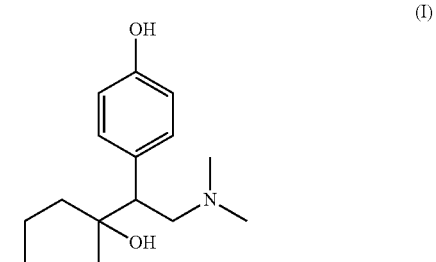

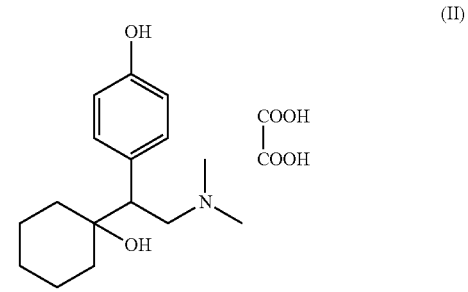

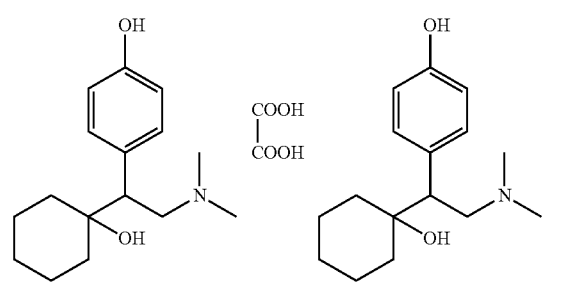

10 Claims, 12 Drawing Sheets

SALTS OF DESVENLAFAXINE AND A METHOD OF THEIR PREPARATION

This application is a National Phase Application of PCT International Application No. PCT/CZ2010/000010, International Filing Date Feb. 3, 2010, entitled "NEW SALTS OF DESVENLAFAXINE AND A METHOD OF THEIR PREPARATION", published on Aug. 12, 2010, as International Publication No. WO 2010/088865, which claims priority from Czech Republic Patent Application No. PV 2009-69, filed Feb. 6, 2009.

TECHNICAL FIELD

The invention deals with new salts of the desvenlafaxine base of formula (I) with oxalic acid, to a method of their preparation and use.

(I)

These new salts are first the hydrogen oxalate of formula (II), i.e. a salt in the desvenlafaxine:oxalic acid proportion of 1:1, (II)

and also the hemioxalate of formula (III), i.e. a salt in the desvenlafaxine:oxalic acid proportion of 2:1.

(III)

BACKGROUND ART

Desvenlafaxine in the form of hydrogen succinate of formula (IV), i.e. a salt with the molar proportion of desvenlafaxine base:succinic acid of 1:1, was approved for treatment of depression and vasomotor symptoms related to the menopause (*Drugs of the Future* 2006, 31(4), 304-309).

(IV)

U.S. Pat. No. 4,535,186 in Example 19 describes preparation of desvenlafaxine by debenzylation of the starting "O-benzyldesvenlafaxine", Scheme 1.

Scheme 1

Desvenlafaxine prepared in this manner in the free base form is transformed by the effect of fumaric acid in an acetone—ethanol mixture to a salt characterized by the melting point of 140-142° C.

Other patented procedures (e.g. U.S. Pat. Nos. 7,026,508, 6,673,838, WO 03/048104, WO 2007/071404, WO 2007/120923) describe preparation of the desvenlafaxine base by demethylation of venlafaxine; Scheme 2. Thiolates or trialkylborohydrides, for example, are used as demethylation agents.

Scheme 2

Venlafaxine

Desvenlafaxine base

Patent no. WO 00/76955 in Example 1 describes transformation of the crude base of Desvenlafaxine to the hydrogen fumarate hydrate of formula (V), i.e. a salt with the molar proportion of desvenlafaxine base:fumaric acid of 1:1: from a methanol/acetone mixture with a small addition of water. The salt is characterized by the melting point of 145-150° C.

U.S. Pat. Nos. 7,026,508 and 6,673,838 mention that the hydrogen fumarate has unsuitable physical and chemical properties, e.g. solubility. For this reason this patent claims the hydrogen succinate, including its several polymorphous forms and hemisuccinate. U.S. Pat. No. 7,001,920 describes preparation of desvenlafaxine formate, which also has more suitable physical and chemical properties than the hydrogen fumarate according to the authors.

DISCLOSURE OF INVENTION

The present invention deals with new salts of desvenlafaxine, which exhibit physical and chemical properties suitable for use as an active pharmaceutical substance. These new salts are the hydrogen oxalate of formula (II), i.e. a salt with the proportion of desvenlafaxine:oxalic acid of 1:1, as well as the hemioxalate of formula (III), i.e. a salt with the proportion of desvenlafaxine:oxalic acid of 2:1.

The invention includes:
(a) Preparation of desvenlafaxine hydrogen oxalate;
(b) Preparation of desvenlafaxine demioxalate;
(c) Re-crystallization of desvenlafaxine hydrogen oxalate;
(d) Re-crystallization of desvenlafaxine hemioxalate;
(e) Use of desvenlafaxine hydrogen oxalate as an active pharmaceutical substance;
(f) Use of desvenlafaxine hemioxalate as an active pharmaceutical substance;

Preparation of a Salt of a Biologically Active Substance Represents the Possibility of Influencing its physical and chemical properties without intervening in the chemical structure. In selection of the crystalline salt the ease and yield of its preparation must be taken into account. It is also necessary to evaluate the properties such as solubility, stability, hygroscopicity, etc. Literature mentions (see e.g. U.S. Pat. No. 6,673,838) that if the solubility of a salt in water is lower than 10 mg/ml, dissolving may represent a speed limiting step during in vivo absorption, which may result in a reduction of biological availability of the active substance. The comparison of biological availabilities of desvenlafaxine hydrogen fumarate and hydrogen succinate mentioned in U.S. Pat. No. 6,673,838, Example 13, may serve as an example. Biological availability demonstrated by absorption of desvenlafaxine in the intestine of a test rat is roughly three times higher in the case of the hydrogen succinate than in the case of hydrogen fumarate.

This result corresponds to our results of measurement of equilibrium solubility as well as dissolution speed of desvenlafaxine hydrogen succinate and hydrogen fumarate. Desvenlafaxine hydrogen succinate dissolves in water approximately twice as fast as the hydrogen fumarate; the equilibrium concentration in water is about 6 times higher in the case of hydrogen succinate than in the case of hydrogen fumarate.

We have surprisingly found out that desvenlafaxine forms stable crystalline salts with oxalic acid both in the proportion of 1:1 (hydrogen oxalate) and in the proportion of 2:1 (hemioxalate), whose physical and chemical properties are considerably different from desvenlafaxine hydrogen fumarate and hydrogen succinate. The salt desvenlafaxine hydrogen oxalate can be generally prepared by mixing of one equivalent of desvenlafaxine base and one equivalent of oxalic acid and subsequent crystallization of the salt. The salt desvenlafaxine hemioxalate can be generally prepared by mixing of two equivalents of desvenlafaxine base and one equivalent of oxalic acid and subsequent crystallization of the salt. Another possibility consists in dissolving of one equivalent of desvenlafaxine hydrogen oxalate and one equivalent of desvenlafaxine base and subsequent crystallization of the salt.

Known salts of desvenlafaxine usually crystallize in the form of hydrates, e.g. the hydrogen fumarate or hydrogen succinate are described as monohydrates. Similarly, the newly prepared desvenlafaxine hydrogen oxalate crystallizes in the form of a hydrate, or rather monohydrate. Desvenlafaxine hemioxalate surprisingly crystallizes not only as a hydrate or dehydrate, but also as an anhydrous salt.

Suitable solvents for the preparation of a salt of desvenlafaxine with oxalic acid and subsequent crystallization include organic solvents with a content of water of 0% to 50% by weight, preferably 0.1 to 25% by weight. Organic solvents suitable for crystallization include the group or C1 to C4 alcohols, C3 to C6 ketones, C4 to C6 ethers or cyclic ethers, or other water-miscible solvents, such as dimethyl sulfoxide or dimethyl formamide. Out of less lipophilic solvents (e.g. methanol or ethanol) these salts can be crystallized without addition of water. In the case of other solvents (e.g. 2-propanol or tetrahydrofuran, dioxan) it is advisable to use an adequate addition of water to achieve an acceptable volume of the solvent and crystallization yield.

The results of measurement of the dehydration temperature by the TGA method and of the melting temperature by the DSC method (Table 1) of desvenlafaxine salts show that the dehydration and meting temperatures are different in the case of oxalates from the other known salts of desvenlafaxine.

TABLE 1

Temperatures of dehydration (TGA) and melting (DSC) of desvenlafaxine salts

| Desvenlafaxine salt | Dehydration temperature (peak) | Melting temperature (peak) |
| --- | --- | --- |
| Base | — | 227° C. |
| Hydrogen fumarate hydrate | 140° C. | 159° C. |
| Hydrogen succinate hydrate | 120° C. | 125° C. |
| Hydrogen oxalate hydrate | 97° C. | 86° C. |
| Hemioxalate, anhydrous | — | 217° C. |
| Hemioxalate, hydrate | 177° C. | 217° C. |

Solubility of the particular form in water is a very important parameter for biological availability of the active substance. It is characterized by equilibrium solubility on one hand, which is defined as the quantity of the substance dissolved in a certain volume in the equilibrium state (the commonly used unit is mg/ml) and the dissolution rate on the other hand, which is defined as the quantity of the substance dissolved from a certain area per certain time unit (i.e. true dissolution, the commonly used unit is mg/cm$^2$/min). In all the new salts of desvenlafaxine with oxalic acid both these characteristics achieve relatively high values, higher than with the previously described salts (Tables 2 and 3). This means that very good solubility in water characterized by high values of the dissolution rate constants and of equilibrium solubilities is a convenient property of these new salts of desvenlafaxine.

TABLE 2

Rate constants of dissolution of desvenlafaxine salts

| Desvenlafaxine salt | Dissolution rate constants at pH 2 (mg/cm$^2$/min) | Dissolution rate constants at pH 6.8 (mg/cm$^2$/min) |
| --- | --- | --- |
| Base | 0.6 | 0.2 |
| Hydrogen fumarate hydrate | 0.8 | 0.8 |
| Hydrogen succinate hydrate | 3.1 | 3.2 |
| Hydrogen oxalate hydrate | 7.1 | 6.0 |
| Hemioxalate, anhydrous | 6.6 | 5.9 |
| Hemioxalate, hydrate | >10 | >10 |

TABLE 3

Equilibrium solubilities of desvenlafaxine salts

| Desvenlafaxine salt | Equilibrium solubility at pH 2 (mg/ml) | Equilibrium solubility at pH 6.8 (mg/ml) |
| --- | --- | --- |
| Base | 2 | 4 |
| Hydrogen fumarate hydrate | 8 | 8 |
| Hydrogen succinate hydrate | 53 | 58 |
| Hydrogen oxalate hydrate | 89 | 63 |
| Hemioxalate, anhydrous | 92 | 80 |
| Hemioxalate, dihydrate | 86 | 71 |

So it is obvious that the new salts of desvenlafaxine with oxalic acid exhibit such physical and chemical properties that make them suitable for use as active pharmaceutical substances. Convenient properties of the salts of desvenlafaxine with oxalic acid mainly include high solubility in water, which is necessary for the preparation of a dosage form with good biological availability. Other convenient properties include chemical and physical stabilities of these salts.

The invention is explained in a more detailed way in the examples below. These examples exclusively have an illustrative character and do not limit the scope of the invention in any aspect.

EXAMPLES OF CARRYING OUT THE INVENTION

Desvenlafaxine base was prepared either by demethylation of venlafaxine in accordance with U.S. Pat. No. 6,673,838, Example 5, or using the procedure described in Examples 1 and 2. Desvenlafaxine hydrogen fumarate was prepared in accordance with WO 00/76955, Example 1. Desvenlafaxine hydrogen succinate was prepared in accordance with U.S. Pat. No. 6,673,838, Example 7.

Example 1

Preparation of Desvenlafaxine Base

O-Benzyldesvenlafaxine base (35 g) is stirred up in MeOH (300 ml). Ammonium formate (25 g) and 3% Pd/C (3.5 g) are added to the solution. The mixture is stirred at 60° C. for 2 hours. The pH of the reaction mixture is adjusted to 5 by addition of formic acid. The mixture is filtered through kieselguhr. The pH value of the filtrate is adjusted to 9.5 by dropwise addition of a 25% aqueous solution of ammonia. The suspension is then stirred at the laboratory temperature for 1 hour and then filtered. The filter cake is washed with water and dried. Yield 25 g (95%); HPLC purity 99.4%.

Example 2

Preparation of Desvenlafaxine Base

O-Benzyldesvenlafaxine base (70 g) is stirred up in MeOH (400 ml) and formic acid (12 ml) is added dropwise. Ammonium formate (25 g) and 10% Pd/C (2 g) are added to the solution. The mixture is stirred at 50° C. for 4 hours. The pH of the solution is adjusted to 5 by addition of formic acid. The mixture is filtered through kieselguhr. The pH value of the filtrate is adjusted to 9.5 by dropwise addition of a 25% aqueous solution of ammonia. The suspension is then stirred at the laboratory temperature for 1 hour and then filtered. The filter cake is washed with water and dried. Yield 49 g (93%); HPLC purity 99.5%.

Example 3

Re-Purification of Desvenlafaxine Base

Desvenlafaxine base (52 G, HPLC purity 99.2%) is stirred up in MeOH (200 Ml) and 2M hydrochloric acid is added dropwise up to the pH value of the solution of 4. The solution is stirred up with activated charcoal and filtered through kieselguhr. The pH value of the filtrate is adjusted to 9.6 by dropwise addition of a 2M solution of sodium hydroxide. The suspension is then stirred at 0° C. for 1 hour and then filtered. The filter cake is washed with water and with cooled 2-propanol. Yield 49 g (94%); HPLC purity 99.9%.

Example 4

Preparation of Desvenlafaxine Hydrogen Oxalate Hydrate

Desvenlafaxine base (11.0 g; 42 mmol) and oxalic acid dihydrate (5.7 g; 45 mmol) are dissolved in a mixture of acetone (100 ml) and water (1 ml) at 50° C. and the almost clear solution is filtered through kieselguhr. Then, another part of acetone (100 ml) is added dropwise and the mixture is slowly cooled down to 0° C. The crystals are aspirated and washed with acetone. Yield 12.9 g (83%). $^1$H NMR (250 MHz. DMSO-d$_6$): 0.96-1.58 (m, 10H, CH$_2$), 2.61 (s, 6H, CH$_3$), 2.93 (dd, 1H, CH), 3.42 (dd, 1H, CH), 3.61 (dd, 1H, CH), 6.73 (d, 2H, Ar), 7.04 (d, 2H, Ar).

Example 5

Preparation of Desvenlafaxine Hemioxalate Trihydrate

Desvenlafaxine base (11.0 g; 42 mmol) and oxalic acid dihydrate (2.52 g; 20 mmol) are dissolved in a mixture of 2-propanol (60 ml) and water (10 ml) at 60° C. and the almost clear solution is filtered through kieselguhr. The mixture is slowly cooled down to 0° C. and stirred for 1 hour. The crystals are extracted and washed with 2-propanol. Yield 7.4 g (56%). $^1$H NMR (250 MHz, DMSO-d$_6$): 0.95-1.53 (m, 10H, CH$_2$), 2.39 (s, 6H, CH$_3$), 2.80-2.96 (m, 2H, CH$_2$), 3.31 (dd, 1H, CH), 6.69 (d, 2H, Ar), 7.11 (d, 2H, Ar).

Example 6

Preparation of Anhydrous Desvenlafaxine Hemioxalate

Desvenlafaxine base (11.0 g; 42 mmol) and oxalic acid dihydrate (2.52 g; 20 mmol) are dissolved in methanol (60 ml) at 50° C. The mixture is slowly cooled down to 0° C. and stirred for 1 hour. The crystals are aspirated and washed with methanol. Yield 10.1 g (78%). $^1$H NMR (250 MHz, DMSO-$d_6$): 0.95-1.53 (m, 10H, $CH_2$), 2.39 (s, 6H, $CH_3$), 2.80-2.96 (m, 2H, $CH_2$), 3:31 (dd, 1H, CH), 6.69 (d, 2H, Ar), 7.11 (d, 2H, Ar).

Example 7

Preparation of Desvenlafaxine Hemioxalate Trihydrate by Re-Crystallization of Anhydrous Desvenlafaxine Hemioxalate Anhydrous desvenlafaxine hemioxalate (6.2 g; 10 mmol) is dissolved in a mixture of 2-propanol (30 ml) and water (3 ml) at 60° C. The mixture is slowly cooled down to 0° C. and stirred for 1 hour. The crystals are aspirated and washed with 2-propanol. Yield 5.8 g (86%).

Example 8

Preparation of Anhydrous Desvenlafaxine Hemioxalate by Re-Crystallization of Desvenlafaxine Hemioxalate Trihydrate Desvenlafaxine hemioxalate trihydrate (6.7 g; 10 mmol) is dissolved in methanol (50 ml) at 50° C. The mixture is slowly cooled down to 0° C. and stirred for 1 hour. The crystals are aspirated and washed with methanol. Yield 5.6 g (90%).

Measurement of the Dissolution Rate

The dissolution rate of desvenlafaxine salts (Table 2) in water at various pH values was measured in a Varian-Vankel System, USP Wood Apparatus (rotary disk method). A disk with the diameter of 5 mm was prepared by compression from about 0.2 g of the substance. Phosphate buffer of pH 6.8 or 0.01 M HCl at 37° C. was used as the aqueous medium. The concentration of the substance in the aqueous solution was measured by the spectrophotometric method using a Varian—Cary 50 apparatus at 217 nm.

Measurement of Equilibrium Solubility

Equilibrium solubility of desvenlafaxine salts (Table 3) was measured after 24-hour stirring of an excess of the salt (about 1 g) in water (10 ml) with various pH at 25° C. and subsequent filtration. Phosphate buffer of pH 6.8 or 0.01 M HCl was used as the aqueous medium. The concentration of the substance in the aqueous solution was measured by the spectrophotometric method using a Varian—Cary 50 apparatus at 227 nm.

X-ray Powder Diffraction

Figure 1:
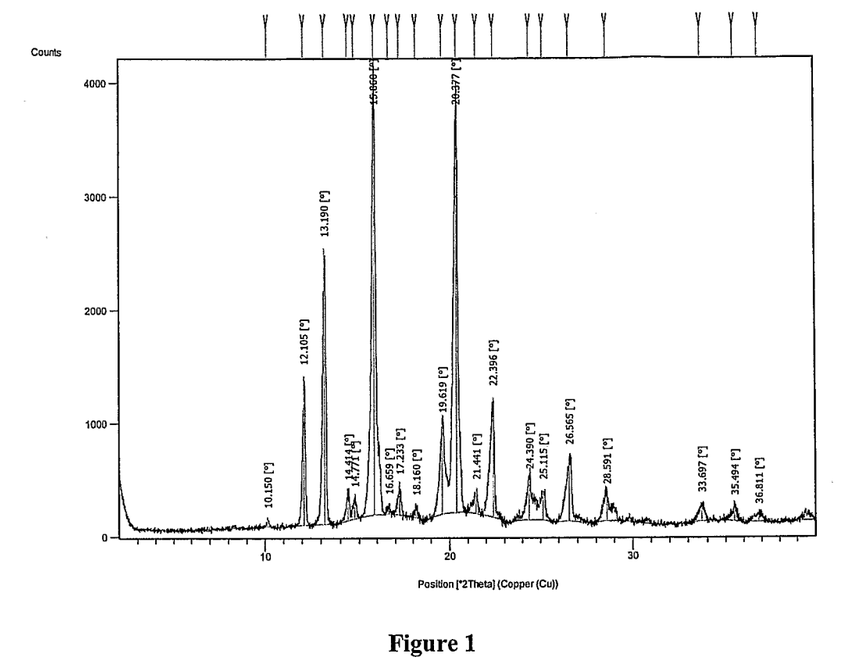
FIG. 1: X-ray diffraction pattern of desvenlafaxine base (characteristic peaks: 12.11; 13.19; 15.86; 20.38 and 22.40° 2θ)
Figure 2:
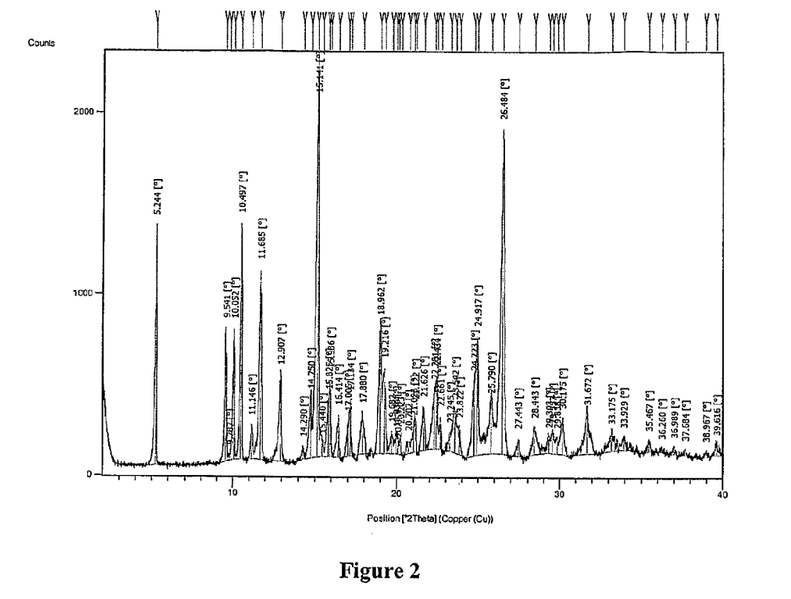
FIG. 2: X-ray diffraction pattern of desvenlafaxine hydrogen oxalate hydrate 1:1, form A
(characteristic peaks: 5.24; 9.54; 10.05; 10.50; 11.69; 15.14; 18.96; 26.48° 2θ)
Figure 3:
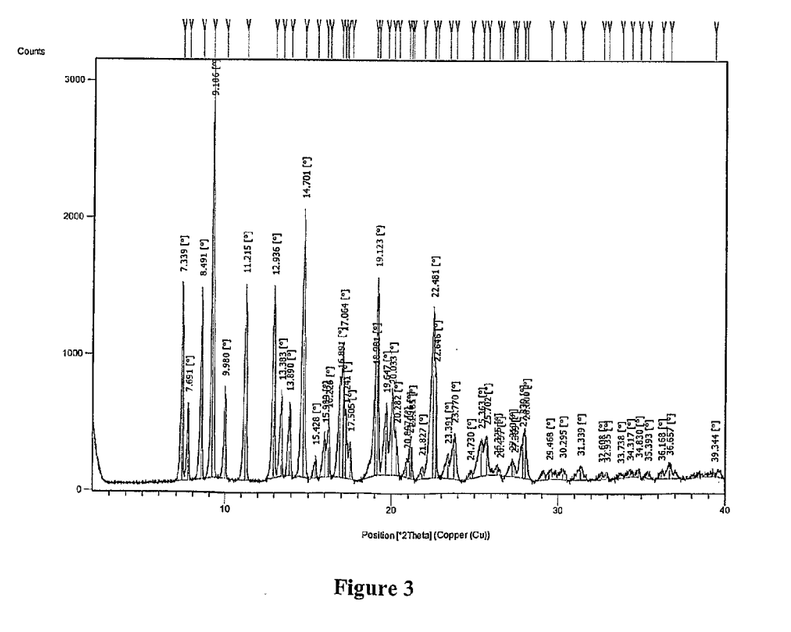
FIG. 3: X-ray diffraction pattern of anhydrous desvenlafaxine hemioxalate 2:1, form B
(characteristic peaks: 7.34; 8.49; 9.19; 11.22; 12.94; 14.70; 17.06; 19.12; 22.48° 2θ)
Figure 4:
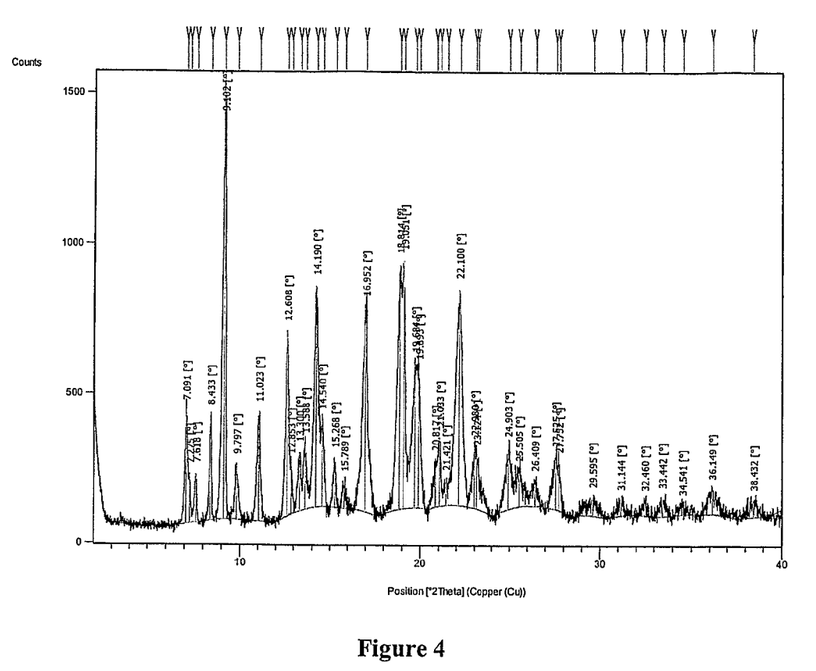
FIG. 4: X-ray diffraction pattern of desvenlafaxine hemioxalate trihydrate 2:1, form C
(characteristic peaks: 7.09; 8.43; 9.10; 11.02; 12.61; 14.19; 16.95; 22.10° 2θ)
Figure 5:
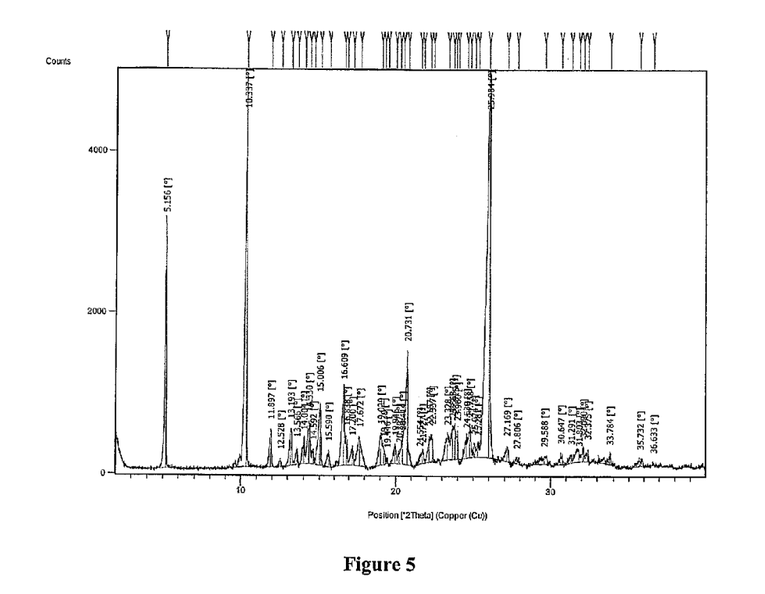
FIG. 5: X-ray diffraction pattern of desvenlafaxine hydrogen succinate
(characteristic peaks: 5.16; 10.34; 15.0; 16.61; 20.73 and 25.98° 2θ)

The presented patterns (FIGS. 1, 2, 3, 4 and 5) were measured with an X'PERT PRO MPD PANalytical diffractometer with a graphite monochromator, radiation used CuKα ($\lambda$=1.542 Å), excitation voltage: 45 kV, anodic current: 40 mA, measurement range: 4-40° 2θ, increment: 0.008° 2θ, irradiated part of the sample 10 mm.

DSC (Differential Scanning Calorimetry)

Figure 6:
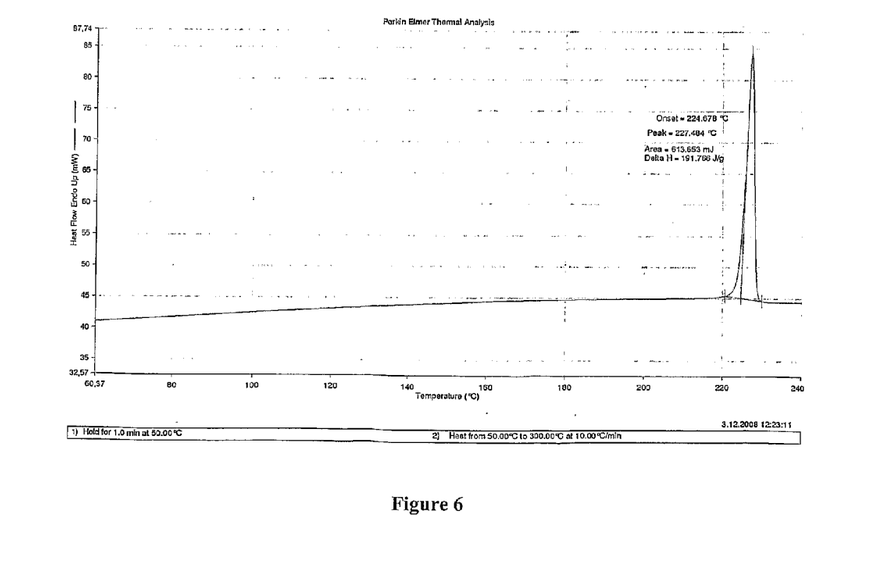
FIG. 6: DSC record of desvenlafaxine base
(characteristic temperatures: Tonset=225° C. and Tpeak=227° C.)
Figure 7:
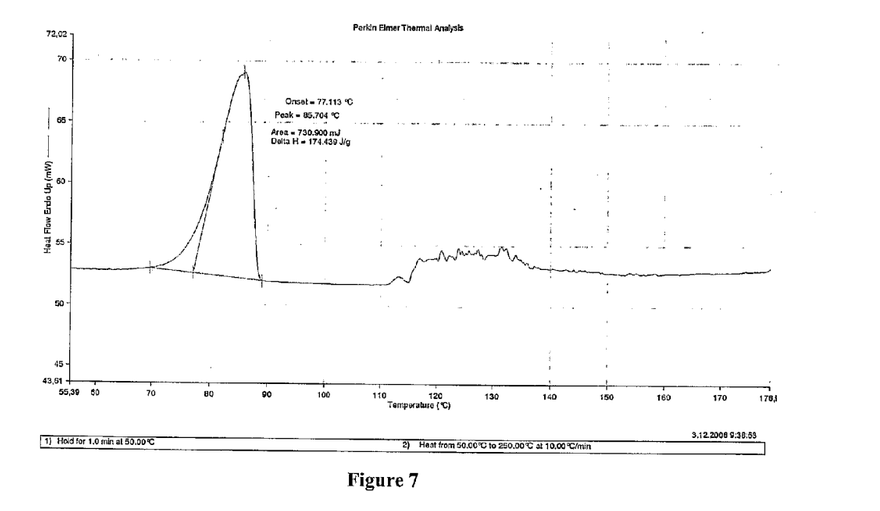
FIG. 7: DSC record of desvenlafaxine hydrogen oxalate hydrate 1:1, form A
Figure 8:
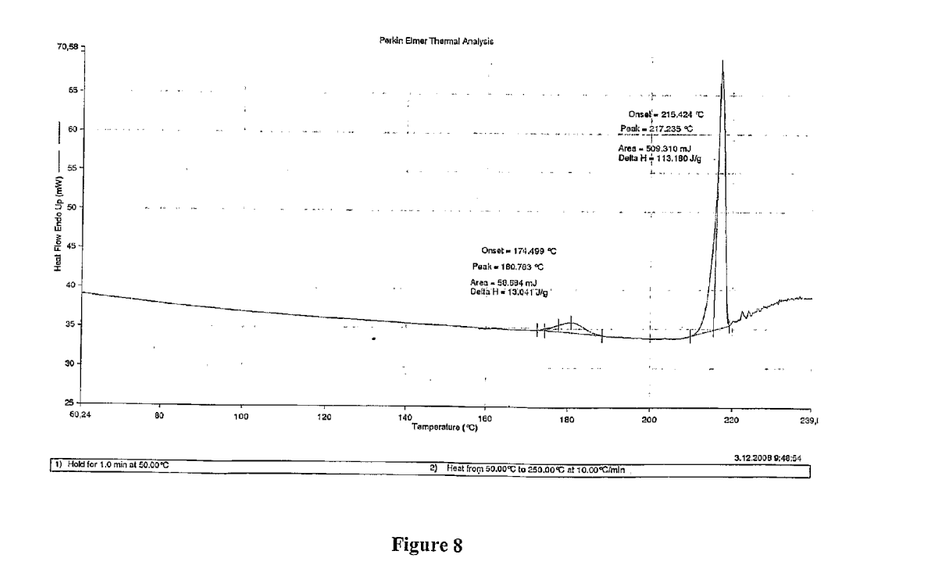
FIG. 8: DSC record of anhydrous desvenlafaxine hemioxalate 2:1, form B
(characteristic temperatures: Tonset1=174° C. and Tpeak1=181° C.; Tonset2=215° C. and Tpeak2=217° C.)
Figure 9:
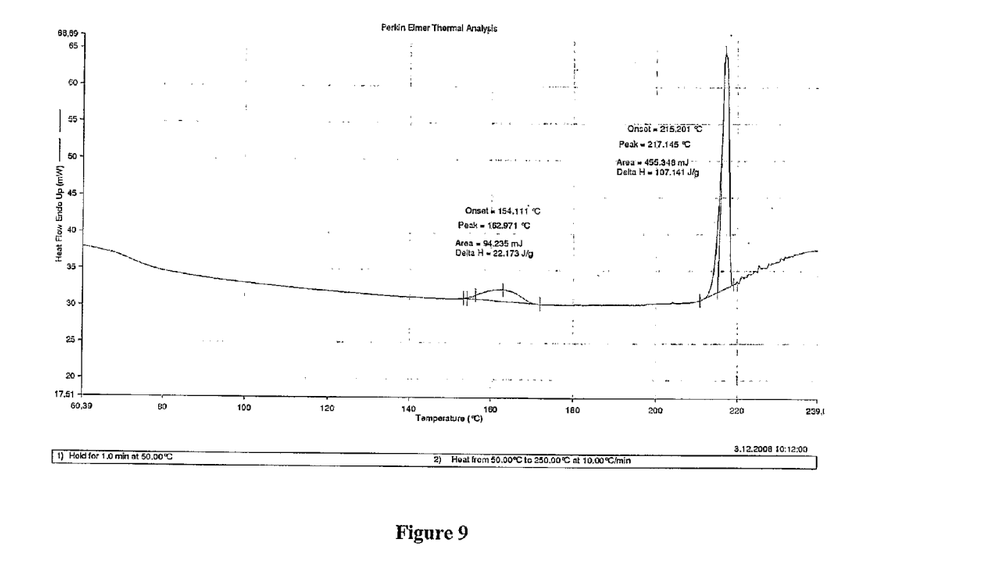
FIG. 9: DSC record of desvenlafaxine hemioxalate trihydrate 2:1, form C
(characteristic temperatures: Tonset1=154° C. and Tpeak1=163° C.; Tonset2=215° C. and Tpeak2=217° C.)
Figure 10:
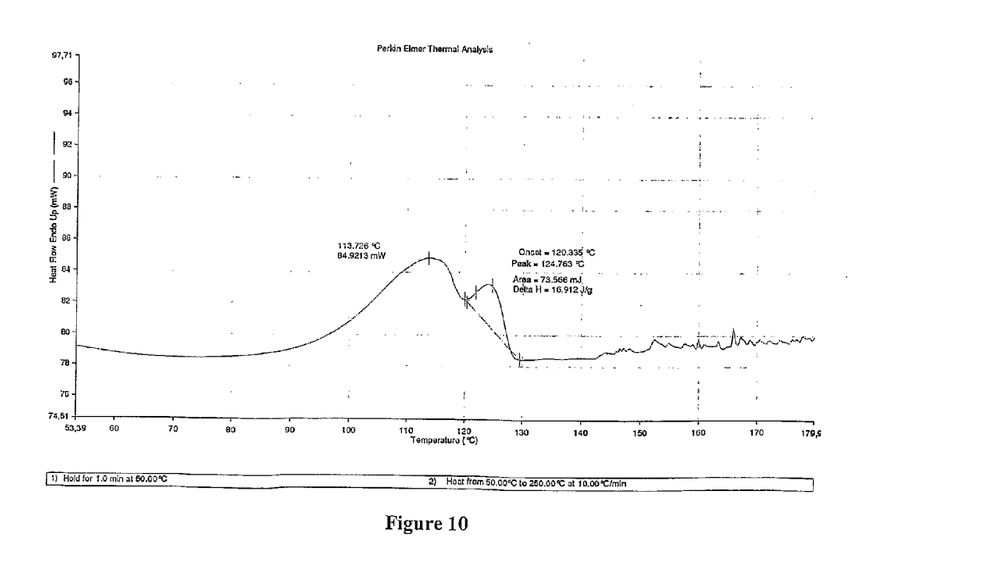
FIG. 10: DSC record of desvenlafaxine hydrogen succinate
(characteristic temperatures: Tonset=120° C. and Tpeak=125° C.)

The presented records (FIGS. 6, 7, 8, 9 and 10) were measured with a Perkin Elmer Pyris 1 apparatus with the sample load of 3 to 5 mm and with heating under nitrogen at the rate of 10° C./min up to the final temperature of 250° C.

TGA (Thermogravimetric Analysis)

Figure 11:
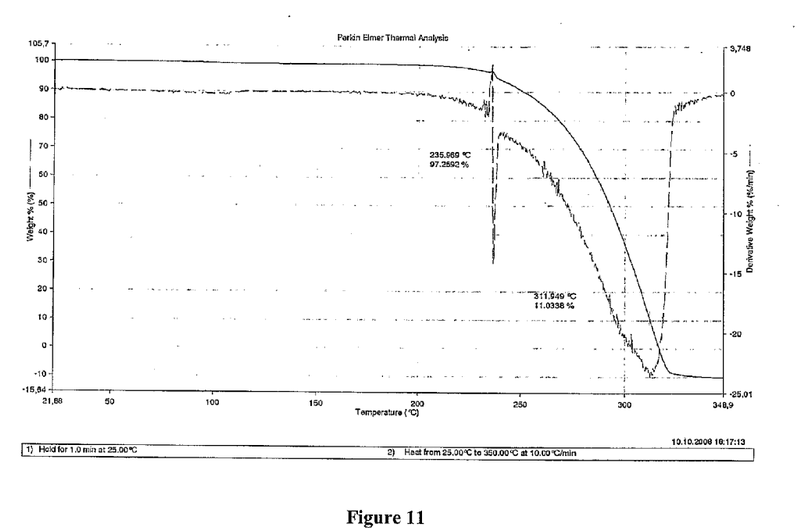
FIG. 11: TG record of desvenlafaxine base
Figure 12:
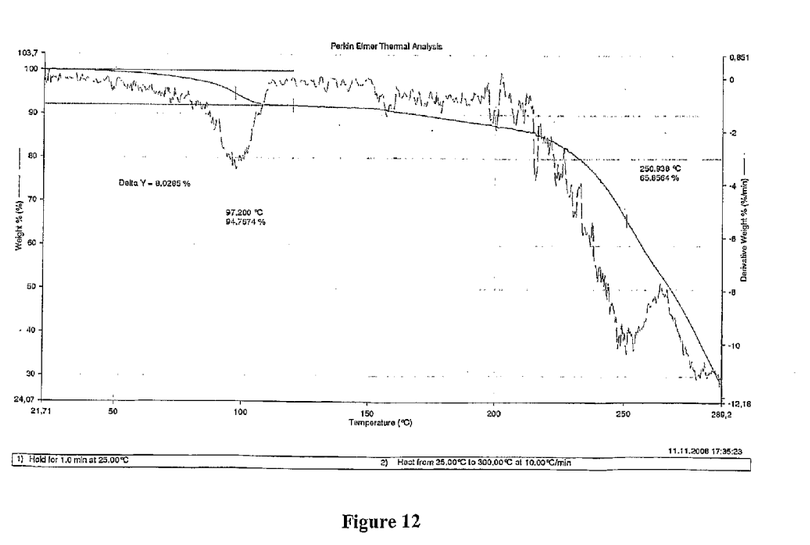
FIG. 12: TG record of desvenlafaxine hydrogen oxalate hydrate 1:1, form A
Figure 13:
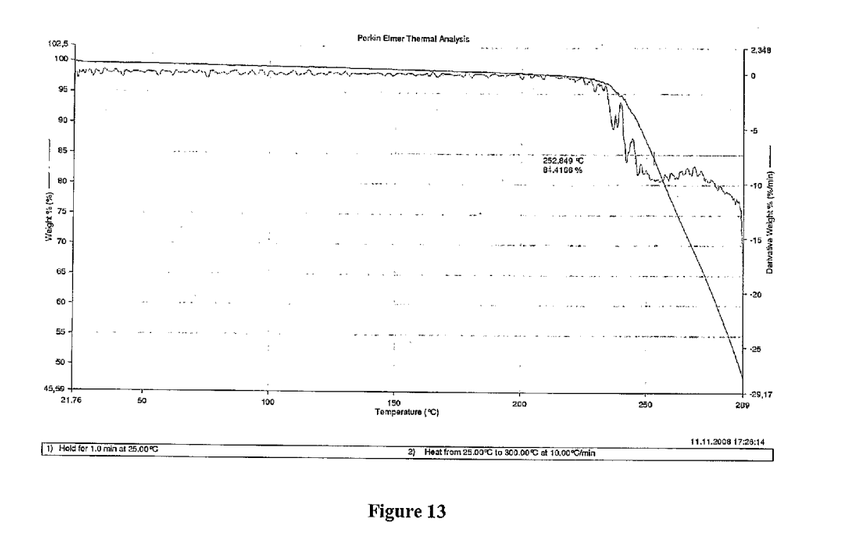
FIG. 13: TG record of anhydrous desvenlafaxine hemioxalate 2:1, form B
Figure 14:
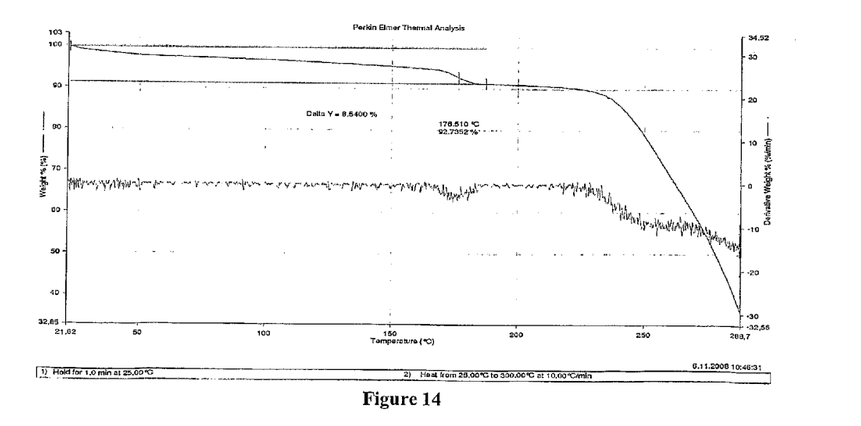
FIG. 14: TG record of desvenlafaxine hemioxalate trihydrate 2:1, form C
Figure 15:
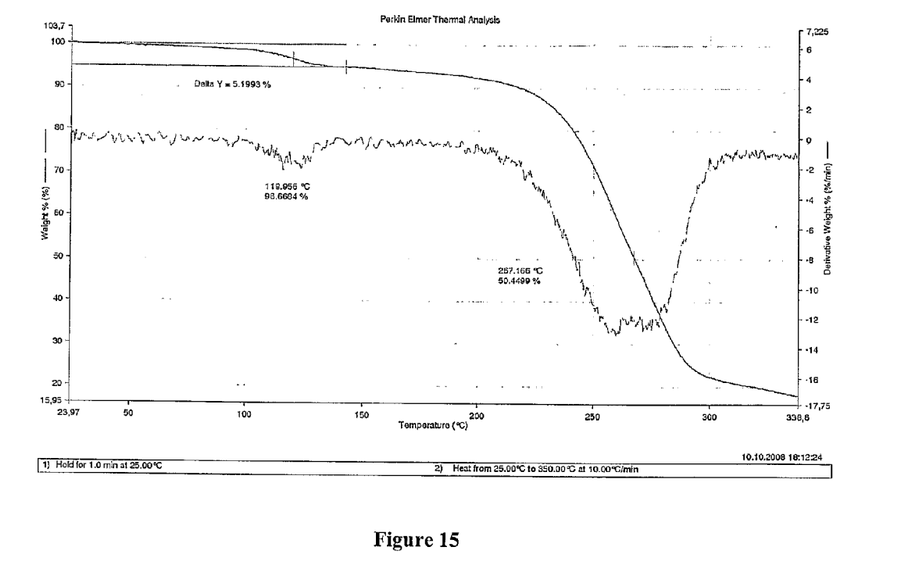
FIG. 15: TG record of desvenlafaxine hydrogen succinate

The presented records (FIGS. 11, 12, 13, 14 and 15) were measured with a Perkin Elmer TGA6 apparatus with the sample load of 10 to 15 mg and with heating under nitrogen at the rate of 10° C./min up to the final temperature of 350° C.

IR (Infrared Spectroscopy)

Figure 16:
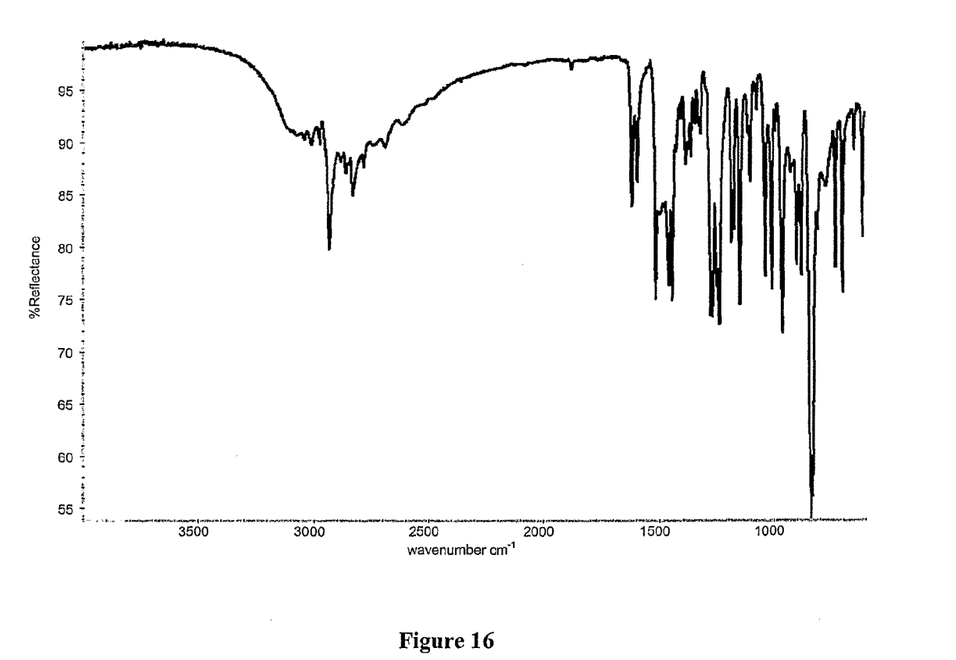
FIG. 16: IR record of desvenlafaxine base
(characteristic bands: ν(CH)+ν(OH) 2936, ν(C=C) 1618, 1594, 1515 cm$^{-1}$)
Figure 17:
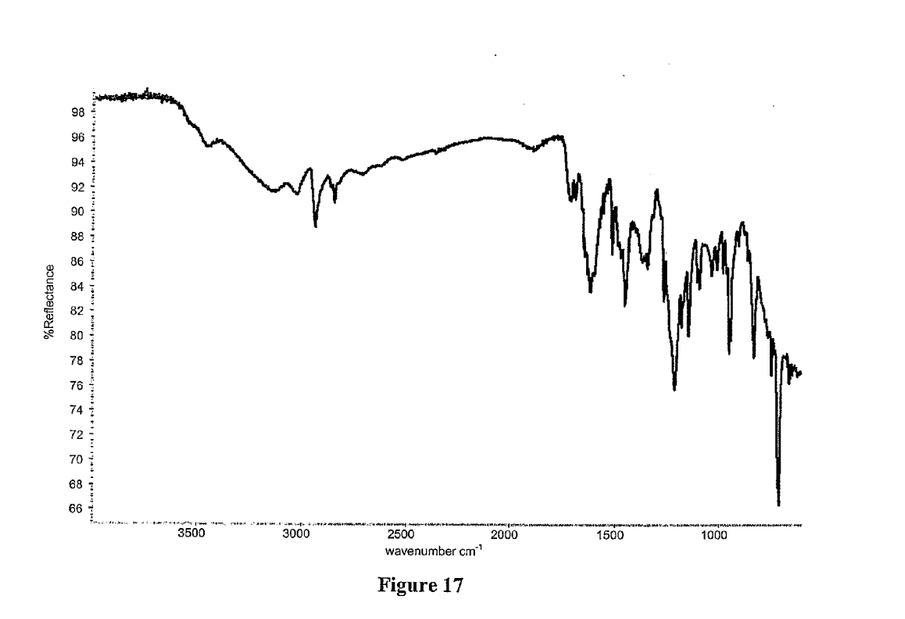
FIG. 17: IR record of desvenlafaxine hydrogen oxalate hydrate 1:1, form A
(characteristic bands: ν(CH)+ν(OH) 2935, ν(C=O) 1709, 1615, ν(C=C) 1516, ν(CO) 1217 cm$^{-1}$)
Figure 18:
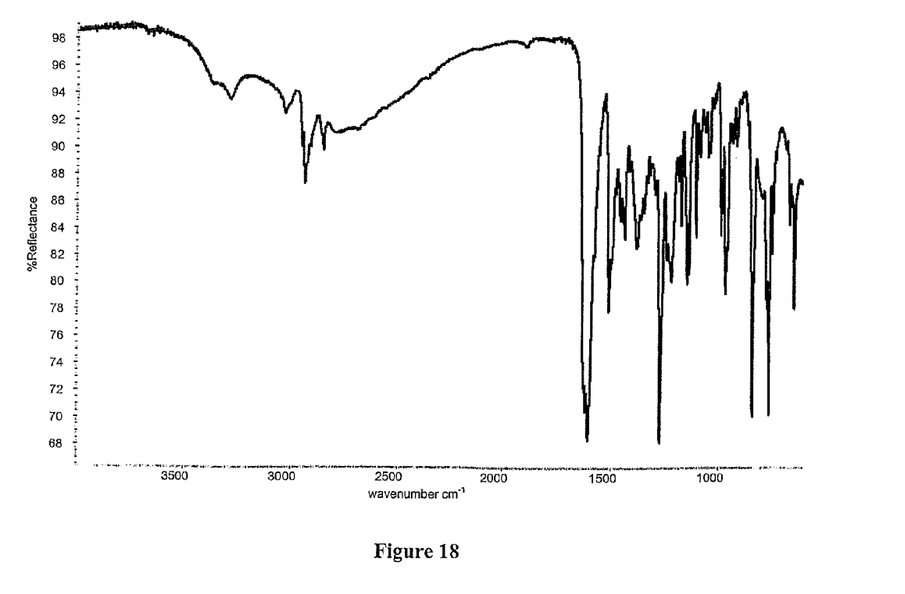
FIG. 18: IR record of anhydrous desvenlafaxine hemioxalate 2:1, form B
(characteristic bands: ν(CH)+ν(OH) 2936, ν(C=O) 1608, ν(C=C) 1515, ν(CO) 1278 cm$^{-1}$)
Figure 19:
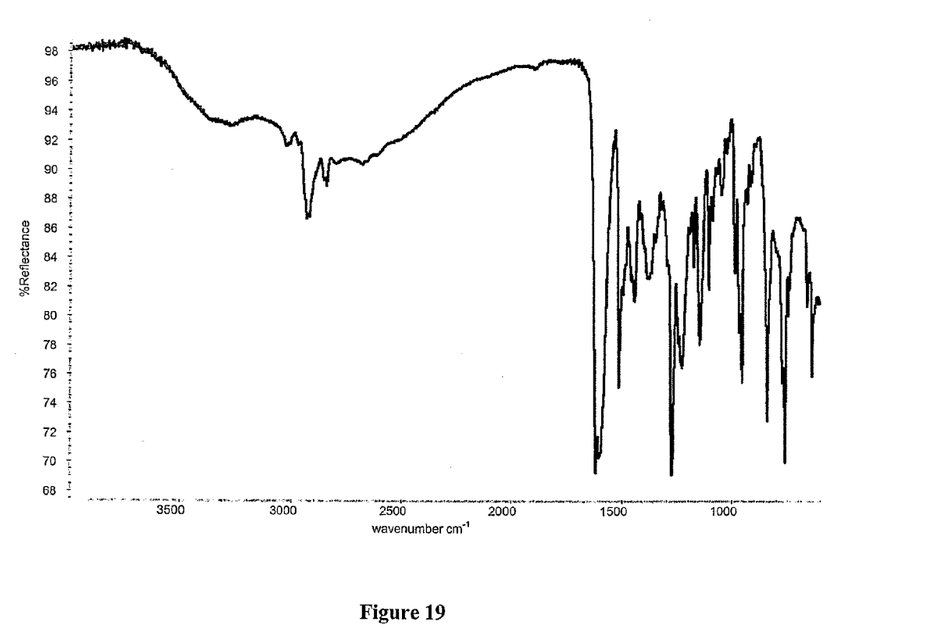
FIG. 19: IR record of desvenlafaxine hemioxalate trihydrate 2:1, form C
(characteristic bands: ν(CH)+ν(OH) 2935, ν(C=O) 1620, ν(C=C) 1515, ν(CO) 1275 cm$^{-1}$)
Figure 20:
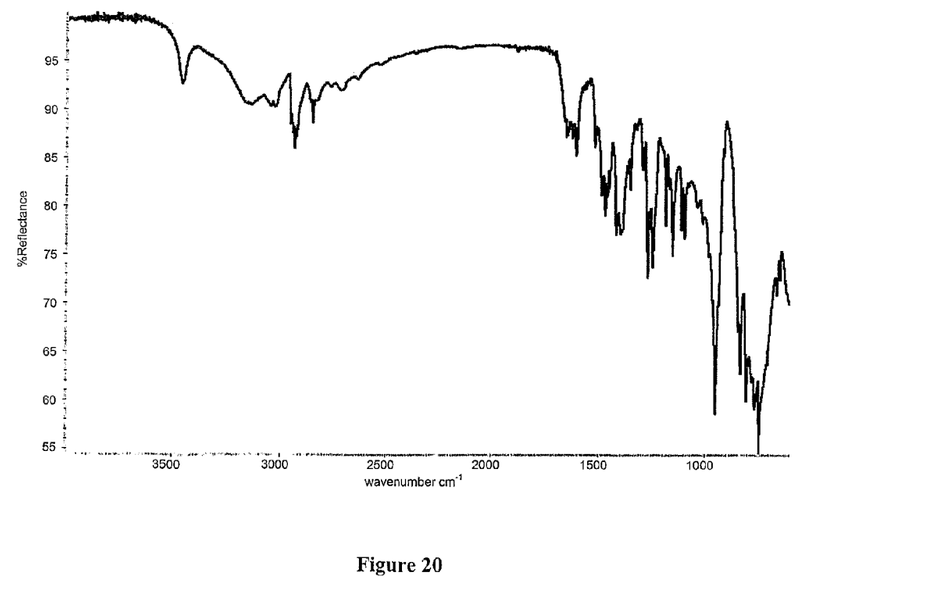
FIG. 20: IR record of desvenlafaxine hydrogen succinate
(characteristic bands: ν(CH)+ν(OH) 2931, ν(C=O) 1651, ν(C=C) 1603, 1516, ν(CO) 1269 cm$^{-1}$)

The presented records (FIGS. 16, 17, 18, 19 and 20) were obtained by accumulation of 64 scans with the resolution of 2 cm$^{-1}$ with an FT-IR Spectrometer Nicolet Nexus apparatus (Thermo, USA).

The invention claimed is:

1. Desvenlafaxine hemioxalate as set forth in formula (III)

(III)

2. The desvenlafaxine hemioxalate according to claim 1, in a hydrate form.

3. The desvenlafaxine hemioxalate according to claim 1, in a trihydrate form.

4. The desvenlafaxine hemioxalate according to claim 1, in an anhydrous form.

5. The desvenlafaxine hemioxalate according to claim 1, having X-ray Powder Diffraction that has the following characteristic peaks: 9.2; 14.7; 19.1; 22.5° 2θ±0.2° 2θ.

6. The desvenlafaxine hemioxalate according to claim 1, having X-ray Powder Diffraction that has the following characteristic peaks: 9.1; 14.2; 17.0; 22.1° 2θ±0.2° 2θ.

7. A method of preparation of desvenlafaxine hemioxalate according to claim 1, comprising the steps of: dissolving 0.9 to 2.1 equivalents of desvenlafaxine and 1 equivalent of oxalic acid in an organic solvent or in a mixture of solvents; cooling or concentrating; and isolating the solid substance.

8. The method according to claim 7, wherein the organic solvent comprises water at 0-50% by weight.

9. The method according to claim 7, wherein the solvent is selected from the group consisting of $C_1$-$C_4$ alcohols and ethers with a content of water of 0-50% by weight.

10. The method according to claim 7, wherein the solvent is selected from the group consisting of tetrahydrofuran, dioxan, methanol, ethanol and 2-propanol with a content of water of 0-25% by weight.

* * * * *